(12) United States Patent
Puschett et al.

(10) Patent No.: US 8,642,568 B2
(45) Date of Patent: Feb. 4, 2014

(54) METHOD OF DIAGNOSING AND THERAPEUTICALLY TREATING A PATIENT FOR A TRAUMATIC BRAIN INJURY

(76) Inventors: Jules B. Puschett, Temple, TX (US); Lee Shapiro, Jarrell, TX (US)

( * ) Notice: Subject to any disclaimer, the term of this patent is extended or adjusted under 35 U.S.C. 154(b) by 0 days.

(21) Appl. No.: 13/160,735

(22) Filed: Jun. 15, 2011

(65) Prior Publication Data

US 2011/0319372 A1 Dec. 29, 2011

Related U.S. Application Data

(60) Provisional application No. 61/358,100, filed on Jun. 24, 2010.

(51) Int. Cl.
*A01N 45/00* (2006.01)
*A61K 31/56* (2006.01)
*A61K 31/58* (2006.01)

(52) U.S. Cl.
USPC .............................. 514/26; 514/170; 514/172

(58) Field of Classification Search
None
See application file for complete search history.

(56) References Cited

U.S. PATENT DOCUMENTS

| 6,726,935 B2 * | 4/2004 | Ji et al. ........................ 424/537 |
| 2011/0008904 A1 | 1/2011 | Puschett | |

FOREIGN PATENT DOCUMENTS

WO    WO 2007/008855    *   1/2007

OTHER PUBLICATIONS

Vu et al. Resibufogenin corrects hypertension in a rat model of human preeclampsia. Experimental Biology and Medicine, 2006, 231: 215-220.*

* cited by examiner

*Primary Examiner* — Anna Pagonakis

(57) ABSTRACT

Known or suspected traumatic brain injuries may be treated therapeutically by administering a therapeutically effective dose of resibufogenin. A preferred method for determining if a patient has a traumatic brain injury includes obtaining a body specimen from the patient, determining the concentration of marinobufagenin in the body specimen, comparing the concentration of marinobufagenin to the concentration in such body specimens in normal patients, and if the marinobufagenin concentration is substantially above the concentration of a normal patient, concluding traumatic brain injury exists. In a preferred embodiment, a substantial elevation is deemed to be an increase of about 30 percent above the marinobufagenin concentration of a normal patient. The body specimen may be blood, urine, or cerebrospinal fluid. If a substantial elevation is deemed to exist, the magnitude of the departure from the concentration of a normal patient may be employed in determining the timing and nature of treatment provided to the patient. The method may be repeated at predetermined intervals to monitor changes in the marinobufagenin with time.

8 Claims, 2 Drawing Sheets

Figure 1
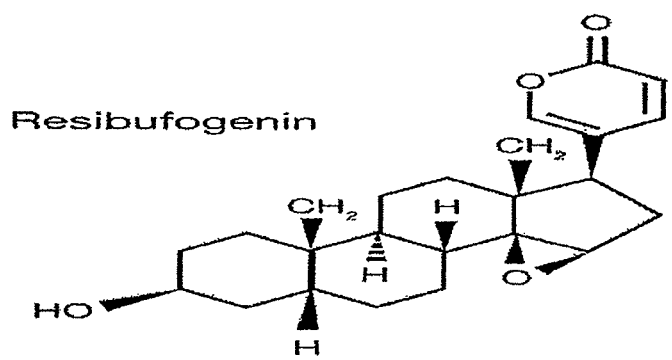
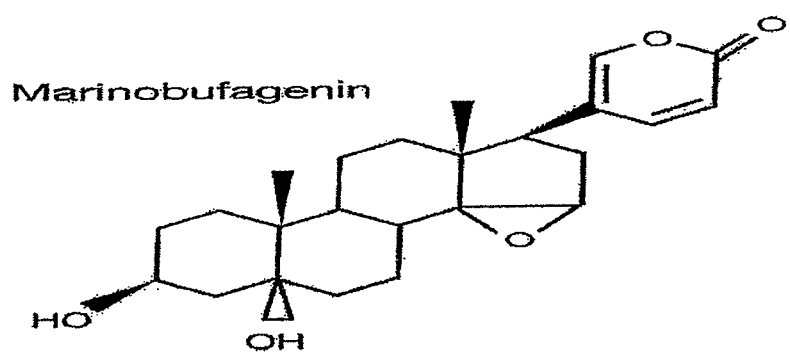
Figure 2

METHOD OF DIAGNOSING AND THERAPEUTICALLY TREATING A PATIENT FOR A TRAUMATIC BRAIN INJURY

BACKGROUND OF THE INVENTION

1. Field of the Invention

The method of this invention relates a method of diagnosing a patient as having a traumatic brain injury and/or treating the patient therapeutically for such traumatic brain injury. In one embodiment, the treatment involves administering a therapeutically effective amount of resibufogenin to the patient.

2. Description of the Prior Art

It has long been known that traumatic brain injuries can result in temporary problems, permanent problems, and in some instances, death. It has, more recently, been recognized that such brain injuries may not, initially, produce symptoms which cause the patient, others, or even medically-skilled individuals to be concerned even though, within a day or two, very serious consequences may result.

In one relatively recent incident, a well-known actress had a minor fall while skiing. She, at the time, felt no adverse consequences and refused medical attention. Several hours later, in her hotel room, she complained of a headache, and within hours, she was in critical condition. She died two days later. As a result of instances such as this, it is important that there be prompt and effective medical attention to situations, wherein traumatic brain injury may have occurred.

At present, one of the rather subjective and not totally effective diagnostic techniques when traumatic brain injury is suspected involves a number of examining techniques. The patient receives a neurological examination which may consist of the following: 1) mental status, 2) motor function, 3) sensory examination, 4) deep tendon reflexes, 5) station, gait, and equilibrium, and 6) cranial nerve function. The mental status examination may include: a) level of consciousness, b) short and long term memory, c) knowledge of patient and place and d) questions about symptoms: headache, dizziness, blurry vision, etc. In addition, the patient may also have radiological studies which could include CT scan of the head, MRI, PET scan. It has been reported that in the early stages of (especially mild) traumatic brain injury, the imaging techniques may not be sufficiently sensitive to detect an abnormality. Furthermore, the patient's cognitive skills may not be impaired initially, and there may be few, if any, symptoms. Patients are often observed over 24-48 hours and are awakened at regular intervals (e.g., every 3-4 hours) to assure that they are able to be aroused. Narcotics for headache or other pain are not given, so that their effects do not cloud the issue of the patient's arousal state. A computerized test which determines level of cognition and reaction time is often employed with repetitive examinations.

One of the problems with this approach in diagnosing potential traumatic brain injuries is that it is not one which always provides precise, timely, objective information. It is also subject to individual variations from person-to-person. Further, if the person is asymptomatic at the time, the conclusion might be that there is no problem, and the individual might be encouraged to go back to normal activities. Such guidance could potentially be injurious to the person's health and could even lead to fatal consequences.

Once a patient has been diagnosed with a traumatic brain injury, it becomes important to treat the patient in a timely, effective manner in order to minimize the risk of permanent injury or death.

In spite of the foregoing known procedures, there remains a very real and substantial need for a method of early and effective determination as to whether an individual has suffered a traumatic brain injury, how severe it might be, and upon finding the presence of such an injury, effectively treating the patient.

SUMMARY OF THE INVENTION

The present invention involves making an initial determination as to whether a patient has a traumatic brain injury. Such a determination may, in one embodiment, be made by the method and apparatus disclosed in U.S. patent application Ser. No. 12/781,464, now U.S. Publication 2011/0008904 A1 (the disclosure of which is expressly incorporated herein by reference) or by other means. Resibufogenin may then be employed as a therapeutic agent in treating the traumatic brain injury to reduce the adverse consequences of the same. Resibufogenin is an antagonist to the actions of marinobufagenin and therefore, interferes with the biological effects of marinobufagenin by virtue of its ability to abrogate many of the cellular actions of marinobufagenin at the molecular level involving MAPK signaling pathways and its effect on apoptosis.

If a substantial elevation in marinobufagenin above that of a normal patient exists, the concentration may be employed in determining the timing and nature of the treatment to be provided to the patient.

In another embodiment of the invention, apparatus for determining the presence of a traumatic brain injury in a patient includes a specimen receiver for receiving a patient's body specimen, such as urine or blood or cerebrospinal fluid, for example. The specimen receiver is structured to employ urine or blood as the body specimen. An analyzer determines the concentration of marinobufagenin in the patient body specimen. This is compared with the concentration in normal patients to determine whether a substantial elevation in marinobufagenin exists in the body specimen obtained from the patient. The presence of a substantial elevation above the normal range is indicative of a traumatic brain injury. In the preferred form, the apparatus may be calibrated to provide an indication that a substantial elevation exists if the elevation of marinobufagenin is at least about 30 percent above the range of normal patients.

It is an object of the present invention to provide a method of accurately and timely treating an individual who has been diagnosed with a traumatic brain injury.

It is an object of the present invention to provide a method of promptly and effectively testing an individual by means of a body specimen to determine if the individual has suffered a traumatic brain injury and to provide subsequent therapeutic treatment to such an individual.

It is another object of the present invention to provide such a method wherein the diagnosis employs blood, either as blood serum or blood plasma, as the body specimen.

It is a further object of the present invention to provide such a method wherein the diagnosis employs urine or cerebrospinal fluid as the body specimen.

It is a further object of the present invention to provide a quantitative determination of a patient's concentration of marinobufagenin in order to determine if a substantial elevation in marinobufagenin in the body specimen, as compared with normal patients, is present, and if a determination that a traumatic brain injury exists, treating the patient with a therapeutically effective dose of resibufogenin.

It is another object of the present invention to treat patients suspected of having a traumatic brain injury.

It is yet another object of the present invention to provide an effective method for early diagnosis of a traumatic brain injury in order to facilitate prompt medical treatment.

It is yet another object of the present invention to provide a reliable, prompt indication of the presence of a traumatic brain injury if such an injury exists even under some circumstances where the prior art approaches would have led to the conclusion that no such problems exist.

It is still a further object of the present invention to provide diagnostic apparatus which may advantageously be employed in processing the body specimen and making a determination regarding the amount of marinobufagenin present in the patient's body specimen.

It is a further object of the present invention to provide such apparatus which will effect a comparison between the marinobufagenin content of the body specimen and that of normal patients.

It is yet another object of the present invention to provide such methods which are employable in connection with battlefield injuries, as well as for civilian uses.

It is a further object of the present invention to repeat periodically the therapeutic administration of resibufogenin.

It is another object of the present invention to monitor the patient's progress utilizing multiple determinations of marinobufagenin over time.

These and other objects of the present invention will be more fully understood in the following detailed description of the invention on reference to the drawings appended hereto.

BRIEF DESCRIPTION OF THE DRAWINGS

FIG. 1 illustrates the chemical structure for resibufogenin.

FIG. 2 illustrates the chemical structure for marinobufagenin.

DETAILED DESCRIPTION OF THE PREFERRED EMBODIMENTS

Figure 3:
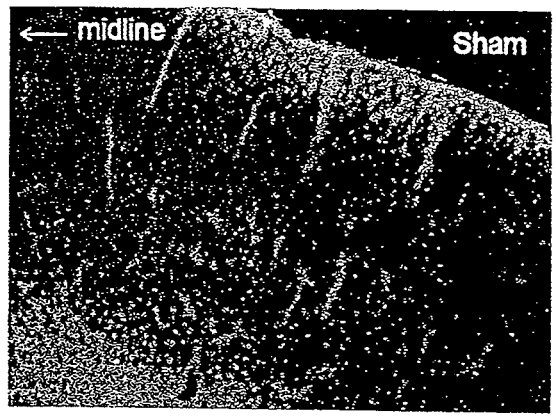
FIG. 3 through 5 represent respectively, representative photomicrographs of three groups of ten rats which have been subjected to the development of traumatic brain injury through impact by a weight under experimental conditions described hereinafter. The image shown in FIG. 3 shows the sham operated rat. The image shown in FIG. 4 shows the rat subjected to impact acceleration injury, and the image shown in FIG. 5 shows the animals which received a 120 µg bolus of resibufogenin 90 minutes after the imposition of brain trauma.

As employed herein, the term "traumatic brain injury" shall mean a brain injury resulting from direct or indirect shock load or loads applied to the brain causing it to move rapidly and unnaturally within a patient's skull and shall expressly include, but not be limited to, brain injuries caused by: (a) objects penetrating the skull, such as, bullets, arrows, and other physical objects which pass through the skull and enter the brain, (b) impact loads applied to the head or other portions of the patient's body, (c) surgically induced trauma, (d) explosions, such as might exist in warfare, through impacting of grenades, bombs, and other explosives, which cause substantial tremors in the earth in relatively-close proximity to where an individual is standing, as well as similar tremors created by nonexplosive means, such as vehicular accidents, collapse of buildings and earthquakes, for example.

As employed herein, the term "normal patient(s)" means a group of non-traumatized subjects matched for age and sex.

The results of traumatic brain injury may be of various types, but in each instance, will involve temporary or permanent reduction in the ability of the brain to function normally and may cause death.

One of the consequences of a traumatic brain injury frequently is the generation of inflammation within the brain as the shock to the brain serves to increase the permeability of the endothelial cells, thereby permitting loss of fluids from the vascular structure into the brain. Such a leakage frequently occurs due to the increased porosity of the blood vessels resulting from the trauma, thereby causing blood serum to leak through the vessels into the brain area. As this builds up, this can generate inflammation and swelling of the brain, which may require surgical intervention.

The diagnostic portion of the present invention may involve measuring a body specimen which may be urine or blood, such as blood serum or blood plasma, or cerebrospinal fluid.

The preferred method involves determining if a patient has a traumatic brain injury by obtaining a body specimen from the patient, determining the concentration of marinobufagenin in the body specimen, and comparing the concentration of marinobufagenin with the marinobufagenin concentration in a similar body specimen in normal patients. If the marinobufagenin concentration is substantially above the concentration of a normal patient, this indicates that a traumatic brain injury exists and therapeutic action is initiated.

The diagnostic means for determining if a traumatic brain injury exists is represented by use of an immuno-fluorescent ELISA assay, for example, to provide the amount of marinobufagenin in the urine, blood or cerebrospinal fluid specimen.

In a preferred embodiment of the present invention, it is determined that a traumatic brain injury exists if the elevation of marinobufagenin is at least about 30 percent over that of a normal patient.

The diagnostic tests and therapeutic treatment may be repeated periodically to determine trends. If the marinobufagenin concentration continues to increase, this reinforces the conclusion that a traumatic brain injury and probably brain cell damage exist. If it decreases, comparison of the concentration with normal patients will facilitate a determination of reduced concern.

As will be seen from a comparison of the chemical structure of resibufogenin in FIG. 1 and chemical structure of marinobufagenin in FIG. 2, the difference between the two compounds is the absence of an hydroxyl group at the β-5 position in the resibufogenin structure.

Figure 4:
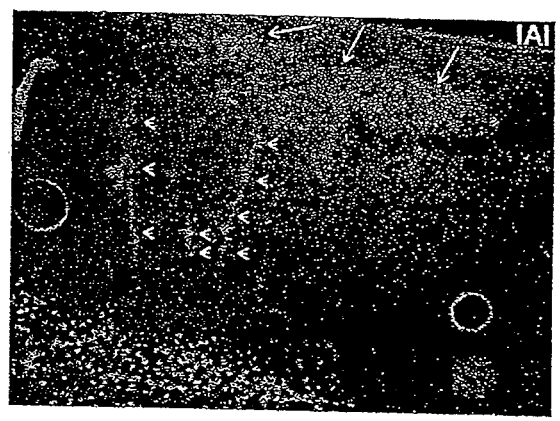
Figure 5:
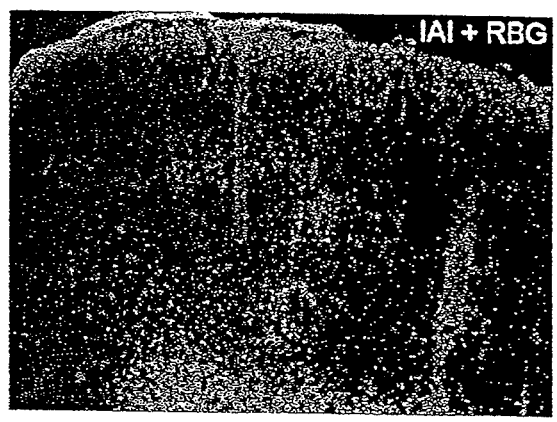

Low and high magnification micrographs of glial fibrillary acidic proteins (GFAP) immuno-fluorescence using a laser-scanning confocal microscope produced FIGS. 3 through 5. The GFAP antibody labels the intermediate filaments of most astrocytes in the brain. These photomicrographs, which were taken 24 hours after the animals were subjected to impact acceleration injury, show areas of cortex slightly lateral to the midline. The pial surface is at the top of the images and the midline is to the left of all images. In the sham animals shown in FIG. 3, a normal distribution of GFAP labeled astrocytes is seen, including their endfeet which surround the neurovasculature. At 24 hours after an impact acceleration injury, as shown in FIG. 4, a noticeable scar is observed as indicated by the plurality of arrows in layers 2 and 3 of the cortex. There is also a patchy loss of GFAP-labeled astrocytes throughout the cortex and the vasculature shown by the arrow heads (as contrasted with the full arrows) appears damaged. It should also be noted that many of the remaining astrocytes appear to be hypertrophied. The loss of all GFAP-immunoreactivity and appearance of astrocyte hypertrophy are indicative of a neuroinflammatory response to injury. As seen in FIG. 5, most of these alterations are ameliorated if the animals are treated with a therapeutically effective dose of resibufogenin at about 90 minutes after the impact acceleration injury. It is important to note that in FIG. 5, there is no observed glial scar. The resibufogenin treatment also functions to reduce the decrease in GFAP immunoreactivity and demonstrates that a greater proportion of GFAP labeled astrocytes have a normal, rather than a hypertrophied appearance.

The resibufogenin may be introduced into the patient by at least one method selected from the group consisting of intravenously, intraperitoneally, intramuscularly, intrathecally, subcutaneously, orally, intraoperatively, topically and during brain surgery by introducing it directly into brain tissue.

Assuming that the initial monitoring of the marinobufagenin indicated that a traumatic brain injury had occurred and treatment with resibufogenin was administered in order to diminish the adverse effect of the traumatic brain injury, one might perform the marinobufagenin test again in an effort to determine the remaining intensity of the traumatic brain injury. This test may be repeated periodically and compared with at least one prior test until the marinobufagenin levels approach or reach the levels of normal patients. Additional doses of resibufogenin may be administered during the course of treatment.

Once the determination that a traumatic brain injury exists has been made, the preferred mode of treatment for a particular patient can be determined. While any suitable means for determining the presence of a traumatic brain injury may be employed, a preferred method is the testing for the marinobufagenin concentration as disclosed herein. The magnitude of increase of marinobufagenin may be employed to influence the timing and nature of the treatment to be provided.

It will be appreciated, therefore, that the present invention provides a method for making a prompt, reliable, and effective determination as to whether an individual is suffering from traumatic brain injury, so as to minimize the risk of an inaccurate diagnosis leading to potentially serious consequences.

It will further be appreciated that the present invention provides a preferred means of treating a patient who has been determined to have a traumatic brain injury. The method of treatment may also be employed for patients suspected of having a traumatic brain injury prior to confirmation that a traumatic brain injury exists. This, in many instances, will serve to reduce the risk of injury to brain tissue. The administration to said patient of a pharmaceutical composition comprising resibufogenin is effective in these circumstances.

EXAMPLE

In order to provide additional information regarding the invention, experiments were performed on animals who were subjected to the impact acceleration injury described hereinbefore, with the animals subsequently being sacrificed and the brains examined 24 hours after the injury. Tests were performed with body specimens which were urinary excretion and also with blood, either blood plasma or blood serum. In each group of ten animals, all had their urine tested and six had blood tested. With the sham animals, the mean urinary excretion values of marinobufagenin were 423±130 (SE)pg-MBG/mg creatinine. With the impact acceleration injury rats, the mean urinary excretion values of marinobufagenin were 3316±1654 MBG/mg creatinine. The corresponding measurements from blood serum showed the sham marinobufagenin values were 33.1±4.2 pg/mL and with impact acceleration injury were 54.5±10.1 pg/mL. These tests confirm the evaluation of marinobufagenin in both urine and blood when an impact acceleration injury is present.

Whereas particular embodiments of the present invention have been described herein for purpose of illustration, it will be evident to those skilled in the art that numerous variations of the details may be made without departing from the invention, as set forth in the appended claims.

What is claimed is:

1. A method of inhibiting glial scar formation associated with traumatic brain injury comprising administering a therapeutically effective dose of resibufogenin to a patient that has suffered a brain injury and has an elevated level of marinobufagenin.

2. The method of claim 1, wherein the level of marinobufagenin in the patient is at least about 30 percent higher than in a normal patient.

3. The method of claim 1, wherein the level of marinobufagenin in the patient is determined using a blood sample from the patient.

4. The method of claim 3, wherein the blood sample is blood serum or blood plasma.

5. The method of claim 1, wherein the level of marinobufagenin in the patient is determined using a urine sample from the patient.

6. The method of claim 1, wherein the level of marinobufagenin in the patient is determined using a cerebrospinal fluid sample from the patient.

7. The method of claim 1, further comprising repeatedly measuring marinobufagenin levels periodically to monitor the progress of the patient.

8. The method of claim 1 wherein resibufogenin is administered by intravenous, intraperitoneal, intramuscular, intrathecal, subcutaneous, oral, topical or intracranial administration.

* * * * *